United States Patent
Colegrove

(10) Patent No.: US 6,509,311 B1
(45) Date of Patent: Jan. 21, 2003

(54) PROPYLENE GLYCOL ALGINATE GELS

(75) Inventor: George Thomas Colegrove, San Diego, CA (US)

(73) Assignee: ISP Investments Inc., Wilmington, DE (US)

( * ) Notice: Subject to any disclaimer, the term of this patent is extended or adjusted under 35 U.S.C. 154(b) by 0 days.

(21) Appl. No.: 09/941,275

(22) Filed: Aug. 28, 2001

(51) Int. Cl.⁷ .............................. A61K 7/46; A61L 9/04; C08J 3/02
(52) U.S. Cl. ........................ 512/4; 516/105; 516/107; 424/76.4; 424/485; 424/488; 514/944
(58) Field of Search .................... 516/105, 107; 424/76.3, 76.4, 485, 488; 514/944; 512/4

(56) References Cited

U.S. PATENT DOCUMENTS

| | | | | |
|---|---|---|---|---|
| 2,735,774 A | * | 2/1956 | Henn | 430/453 |
| 3,351,581 A | * | 11/1967 | Schweiger | 536/2 |
| 3,736,149 A | * | 5/1973 | Knapp | 426/103 |
| 5,026,735 A | * | 6/1991 | Stern | 252/3 |
| 5,192,566 A | * | 3/1993 | Cox et al. | 426/104 |

FOREIGN PATENT DOCUMENTS

EP 0 537 999 A2 * 4/1993

* cited by examiner

*Primary Examiner*—Daniel S. Metzmaier
(74) *Attorney, Agent, or Firm*—Walter Katz; William J. Davis; Marilyn J. Maue

(57) ABSTRACT

A gel system comprising propylene glycol alginate and basic aluminum acetate salt. Also, disclosed is a personal care formulation comprising a room deodorant gel employing said gel system.

10 Claims, No Drawings

PROPYLENE GLYCOL ALGINATE GELS

BACKGROUND OF THE INVENTION

1. Field of the Invention

This invention relates to alginate gels, and, more particularly, to alginate gel systems of propylene glycol alginate and an aluminum salt as the gelling agent.

2. Description of the Prior Art

Alginate has been used for many years as a gelling agent in puddings, fruit fillings, dessert gels, and structured foods, as a water binder in frozen foods, pastry fillings syrups, and icings, as an emulsifier in salad dressings and meat flavor sauces, and as a stabilizer in beer, fruit juice, toppings, sauces and gravies.

Representative of the alginate gel art are the following U.S. Pat. Nos. 2,441,720; 2,918,375; 3,060,032; 3,352,688; 3,770,462; and EP 345886.

Propylene glycol alginates are esters of alginic acid which are commercially available with various degrees of esterification ranging from about 40% to about 90% ester. These alginates are used in such products as salad dressings, and for stabilization of beer foam, where an acid pH is present. However, such alginates have not been considered for gel formation, or for the production of useful gels.

SUMMARY OF THE INVENTION

What is described herein is a gel system comprising propylene glycol alginate and an aluminum salt, preferably a sparingly water soluble aluminum salt, and, most preferably basic aluminum acetate.

In a preferred embodiment of the invention, the propylene glycol alginate is esterified in the range 40–90%, and is present in an amount of about 0.5–5.0 wt. %, preferably about 1.0–2.5 wt. %.

In the gel system herein, the aluminum concentration preferably is in the range 20–100% of complete reaction with the carboxyl groups of the alginate, most preferably about 35–75% of complete reaction. A nonionic polymeric viscosifier also may be included therein, particularly if excess aluminum ions are present.

As a feature of the invention, there is provided a process of making such a gel system by adding an aqueous slurry of the aluminum salt to the propylene glycol alginate, suitably at ambient temperature.

A dry blend of the gel system components is provided herein for suitable dispersion in an aqueous media with agitation to form the desired gel system.

Another feature herein is the provision of a formulation including the above-described gel system, such as a personal care formulation.

DETAILED DESCRIPTION OF THE INVENTION

In this invention, the combination of propylene glycol alginate and an aluminum salt, preferably a sparingly soluble aluminum salt, such as basic aluminum acetate, $Al(OH)(C_2H_3O_2)_2$, provides a useful range of gels, whose characteristics will depend upon the degree of esterification of the alginate and the amount of aluminum salt used. Gel textures ranging from soft and elastic to firm and rigid can be made herein as the components are varied. For example, propylene glycol alginates with a high degree of esterification generally will produce soft, elastic gels while a lower degree of esterification will provide firm, brittle gels.

Advantageously, in this invention, gelation does not occur immediately so that a sequestrant is not needed to slow down the rate of reaction, as in previous alginate gel systems. Actually, the aluminum salt may be added to the alginate in an aqueous medium and the resulting solution filled into a container before gelation occurs. Reaction of the propylene glycol alginate with the sparingly soluble aluminum salt is slowed down herein by the presence of the ester group in the alginate so that some period of time is required to build-up the gel structure. In this manner, a very desirable uniform gel is obtained.

In the preferred forms of the invention, the propylene glycol alginate is esterified to about 40–90%; its concentration in the aqueous gel system is about 0.5–5.0 wt. %, most preferably 1–2.5 wt. %; and the aluminum salt concentration will provide 20–100% of complete reaction with the carboxyl groups of the alginate, most preferably 35–75%.

The invention will be described in more detail with reference to the following examples.

Preparation of Gel Systems of Invention

EXAMPLE 1

4.0 g of Kelcoloid LVF, a low viscosity, 50–59% esterified, propylene glycol alginate (ISP Alginates, San Diego, Calif.) was dissolved in 190 g of deionized water. Then a slurry of 0.27 g of basic aluminum acetate about 50% of theoretical for complete reaction with free carboxyl groups present in the alginate in deionized water was then added and mixed thoroughly. The amount of added basic aluminum acetate was a soft elastic gel formed after an hour; which, upon standing over a period of 24 hours gradually changed into a firm, brittle gel.

EXAMPLE 2

Example 1 was repeated using Manucol Ester M, a medium viscosity propylene glycol alginate, having a degree of esterification of 52–56%. A gradual gelation to a firm, stable gel occurred in like manner.

EXAMPLE 3

Example 1 was repeated using Kelcoloid S, a low viscosity, highly esterified (82–85%) propylene glycol alginate. A very soft, elastic gel was formed.

EXAMPLE 4

Example 1 was repeated using Kelcoloid HVF, a high viscosity product with a degree of esterification of abut 45–50%. A very firm stable gel gradually formed which showed no syneresis or bleeding even after several days.

EXAMPLE 5

Example 1 was repeated with 4.0 g of Kelcoloid LVF was dissolved in 190 g of deionized water to which a slurry of 0.54 g of basic aluminum acetate (100% of theoretical) in 6.0 g of water was added. A soft gel formed in about 45 minutes which gradually changed into a very firm, brittle gel which showed gel syneresis, indicating gel instability.

EXAMPLE 6

Example 1 was repeated with 4.0 g of Kelcoloid LVF was dissolved in 190 g of deionized water to which a slurry of 0.11 g of basic aluminum acetate in 6.0 g of water was added, (20% of theoretical). A soft elastic gel was formed.

Preparation of Personal Care Formulations Using
Gel System of Invention

EXAMPLE 7

A stable, room deodorant gel was prepared according to the following formulation:

| Kelcoloid LVF | 4.0 g | (ISP Alginates) |
|---|---|---|
| Deionized water | 184 | |
| Tween 80 | 1.9 | (Van Waters & Rogers) |
| Mint Oil | 5.0 | (Givaudan) |
| Basic aluminum acetate | 0.27 | (EM Science) |
| Water | 6.0 | |

The formulation was prepared under ambient temperature conditions.

The propylene glycol alginate was dissolved in 184 g water containing Tween 80 and mint oil. After complete dissolution, the aluminum salt was added as a slurry in the remaining water and mixed thoroughly. The formulation was then poured into containers where gelation occurred. The gel was stable and released the mint oil fragrance in the same manner as present commercially available products made with carrageenan or gellan gum.

Alternatively, a dry blend of propylene glycol alginate and the aluminum salt admixture may be used for subsequent, dispersion in aqueous media with rapid agitation to provide the desired gel system.

To improve syneresis control of the gel system herein, e.g. in situations where an excess of aluminum ions may be present therein, the addition of a nonionic polymeric viscosifier to the mixture is advantageous. Suitable polymers include guar gum, hydroxypropyl methylcellulose and hydroxyethylcelulose. Guar gum is a preferred polymer, e.g. present in an amount of about 0.25–1.0% by weight of the system.

While the invention has been described with particular reference to certain embodiments thereof, it will be understood that changes and modifications may be made which are within the skill of the art. Accordingly, it is intended to be bound only by the following claims, in which.

What is claimed is:

1. A gel system comprising propylene glycol alginate having a degree of esterification in the range of 40–90% and a sparingly soluble aluminum salt; and optionally a nonionic polymeric viscosifier; and wherein said aluminum salt is basic aluminum acetate in the range of 20–100% of complete reaction with the carboxyl groups of the alginate and said gel is made in the absence of a sequestrant.

2. A gel system according to claim 1 wherein the propylene glycol alginate concentration is about 0.5–5.0 wt. %.

3. A gel system according to claim 2 wherein said propylene glycol alginate concentration is about 1.0–2.5 wt. %.

4. A gel system according to claim 1, wherein the aluminum concentration is about 35–75%.

5. A gel system according to claim 1 including a nonionic polymeric viscosifier.

6. A gel system according to claim 5 in which said polymer is guar gum present in an amount of about 0.25–1% by weight of the system.

7. A personal care formulation including the gel system of claim 1.

8. A process of making the gel system of claim 1 which comprises aqueous slurry of the aluminum salt to the propylene glycol alginate.

9. A process according to claim 8 which is carried out at ambient temperature.

10. A dry blend suitable for forming a gel system in an aqueous media comprising propylene glycol alginate having a degree of esterification in the range of 40–90% and a sparingly soluble aluminum salt; and optionally a nonionic polymeric viscosifier; and wherein said aluminum salt is basic aluminum acetate in the range of 20–100% of complete reaction with the carboxyl groups of the alginate and is free from sequestrants.

* * * * *